United States Patent
Yamada et al.

(10) Patent No.: US 10,751,552 B2
(45) Date of Patent: Aug. 25, 2020

(54) TUMOR TRACKING APPARATUS AND IRRADIATION SYSTEM

(71) Applicants: HITACHI, LTD., Tokyo (JP); NATIONAL UNIVERSITY CORPORATION HOKKAIDO UNIVERSITY, Sapporo-shi, Hokkaido (JP)

(72) Inventors: Takahiro Yamada, Tokyo (JP); Toru Umekawa, Tokyo (JP); Yusuke Fujii, Sapporo (JP); Naoki Miyamoto, Sapporo (JP); Kikuo Umegaki, Sapporo (JP)

(73) Assignees: HITACHI, LTD., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 54 days.

(21) Appl. No.: 16/088,534

(22) PCT Filed: Mar. 30, 2017

(86) PCT No.: PCT/JP2017/013173
§ 371 (c)(1),
(2) Date: Sep. 26, 2018

(87) PCT Pub. No.: WO2017/187877
PCT Pub. Date: Nov. 2, 2017

(65) Prior Publication Data
US 2019/0111282 A1 Apr. 18, 2019

(30) Foreign Application Priority Data
Apr. 26, 2016 (JP) .................. 2016-088163

(51) Int. Cl.
*A61N 5/10* (2006.01)
*A61B 6/12* (2006.01)
*A61B 6/02* (2006.01)
*A61B 6/00* (2006.01)

(52) U.S. Cl.
CPC ............ *A61N 5/1049* (2013.01); *A61B 6/022* (2013.01); *A61B 6/12* (2013.01); *A61B 6/5211* (2013.01);
(Continued)

(58) Field of Classification Search
None
See application file for complete search history.

(56) References Cited

U.S. PATENT DOCUMENTS

| 6,307,914 B1 | 10/2001 | Kunieda et al. |
| 2002/0167552 A1 | 11/2002 | Senda |

(Continued)

FOREIGN PATENT DOCUMENTS

| CN | 103269752 A | 8/2013 |
| JP | 63-92336 A | 4/1988 |

(Continued)

OTHER PUBLICATIONS

Korean Office Action received in corresponding Korean Application No. 10-2018-7027719 dated Sep. 30, 2019.

(Continued)

*Primary Examiner* — Hoon K Song
(74) *Attorney, Agent, or Firm* — Mattingly & Malur, PC

(57) ABSTRACT

A tumor tracking control device (41) performs windowing process on a captured image A (61) and a captured image B (62), measures a position of a marker (29) using the captured image A (61) and the captured image B (62) after performing the windowing process, and generates a signal capable of controlling irradiation with radiation based on the position of the marker (29). Accordingly, it is possible to provide a (Continued)

tumor tracking apparatus and an irradiation system which are capable of tracking an object to be tracked without erroneous detection, even in a case where a structure similar to the object to be tracked is in the vicinity of the object to be tracked, in tumor tracking.

10 Claims, 8 Drawing Sheets

(52) U.S. Cl.
CPC .... *A61N 5/1067* (2013.01); *A61N 2005/1061* (2013.01); *A61N 2005/1074* (2013.01)

(56) References Cited

U.S. PATENT DOCUMENTS

| | | |
|---|---|---|
| 2009/0052760 A1 | 2/2009 | Smith et al. |
| 2013/0083895 A1 | 4/2013 | Umekawa et al. |
| 2013/0274539 A1 | 10/2013 | Yamada et al. |
| 2014/0371513 A1* | 12/2014 | Maurer, Jr. ......... G06F 19/3481 600/1 |
| 2018/0140260 A1* | 5/2018 | Taguchi ................ A61B 6/022 |

FOREIGN PATENT DOCUMENTS

| | | |
|---|---|---|
| JP | 3053389 B | 6/2000 |
| JP | 2004-32974 A | 11/2004 |
| JP | 2013-78479 A | 5/2013 |
| JP | 2014-054302 A | 3/2014 |
| WO | 2014/041909 A1 | 3/2014 |

OTHER PUBLICATIONS

Chinese Office Action received in corresponding Chinese Application No. 201780019405.1 dated Dec. 4, 2019.
International Search Report of PCT/JP2017/013173 dated Jun. 13, 2017.

\* cited by examiner

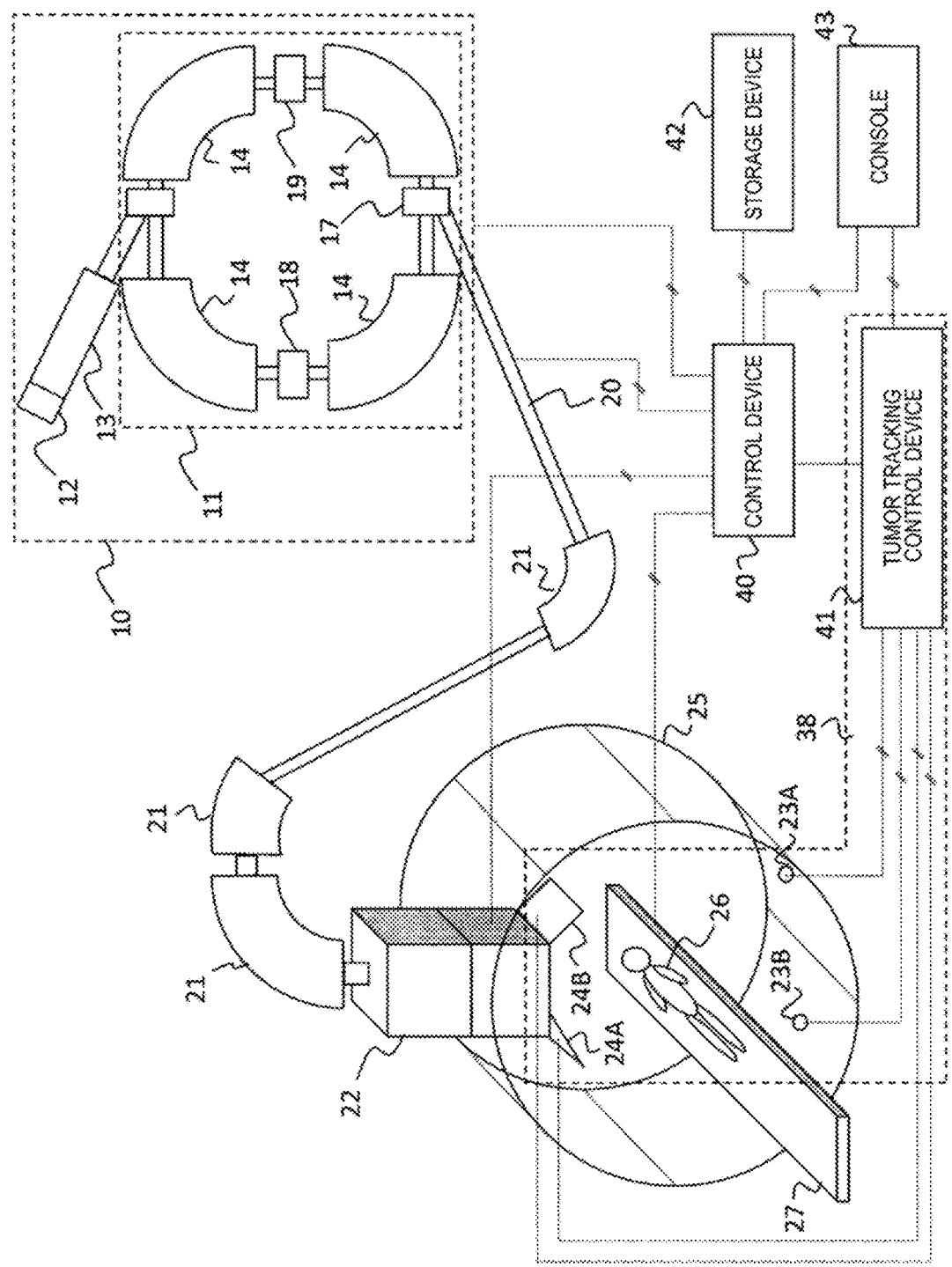
[FIG. 1]

[FIG. 2]
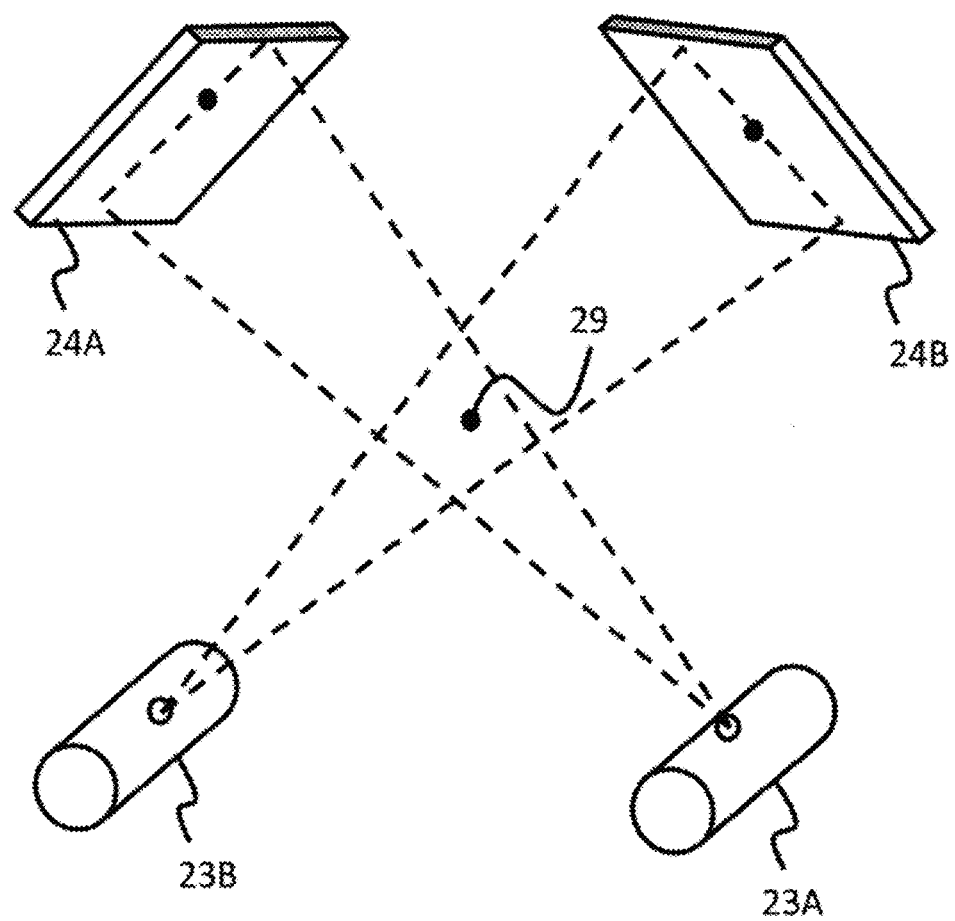

[FIG. 3]
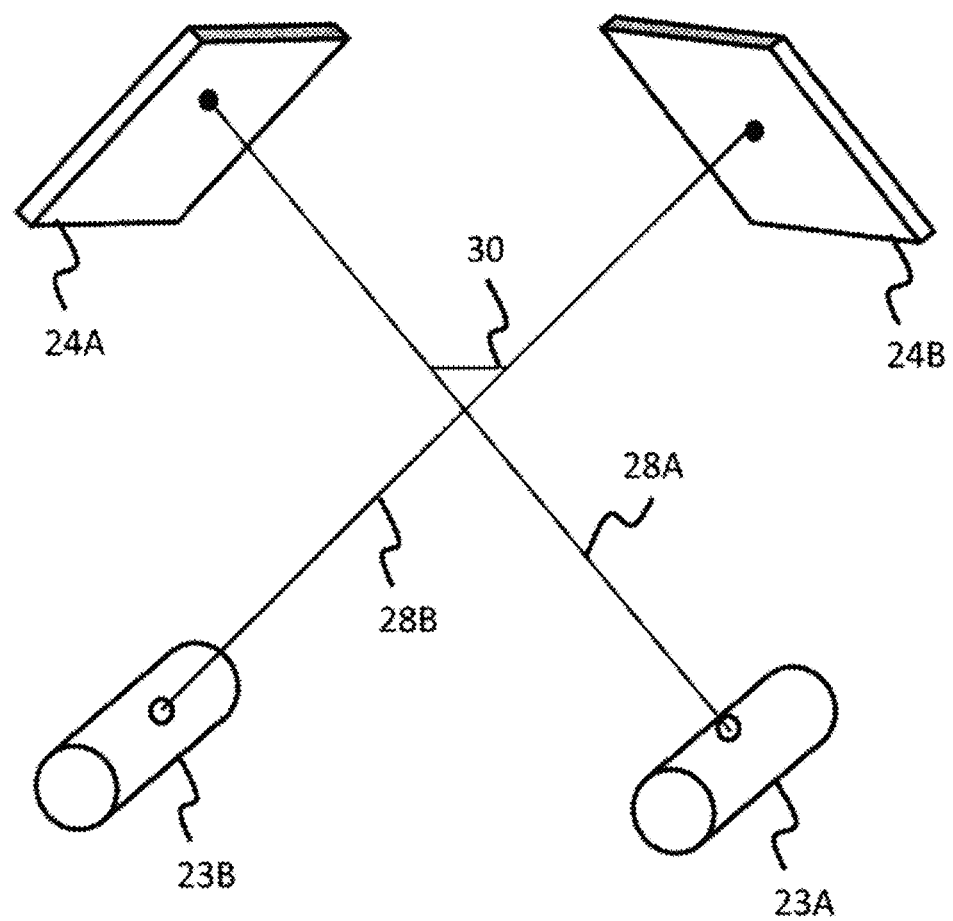

[FIG. 4A]
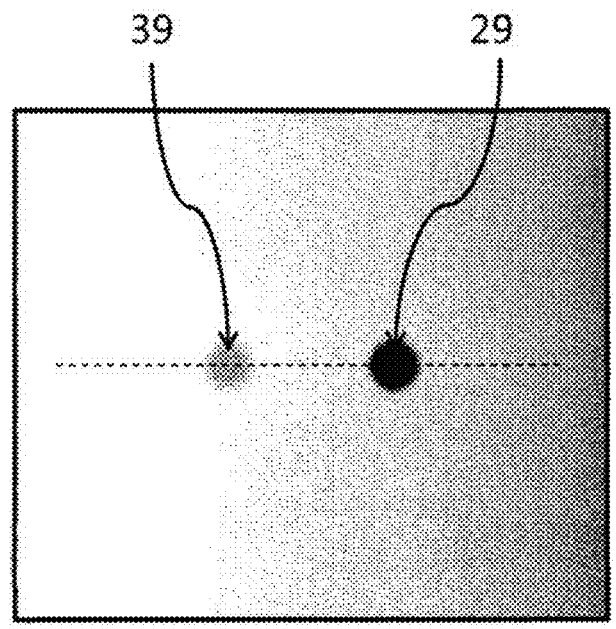

[FIG. 4B]
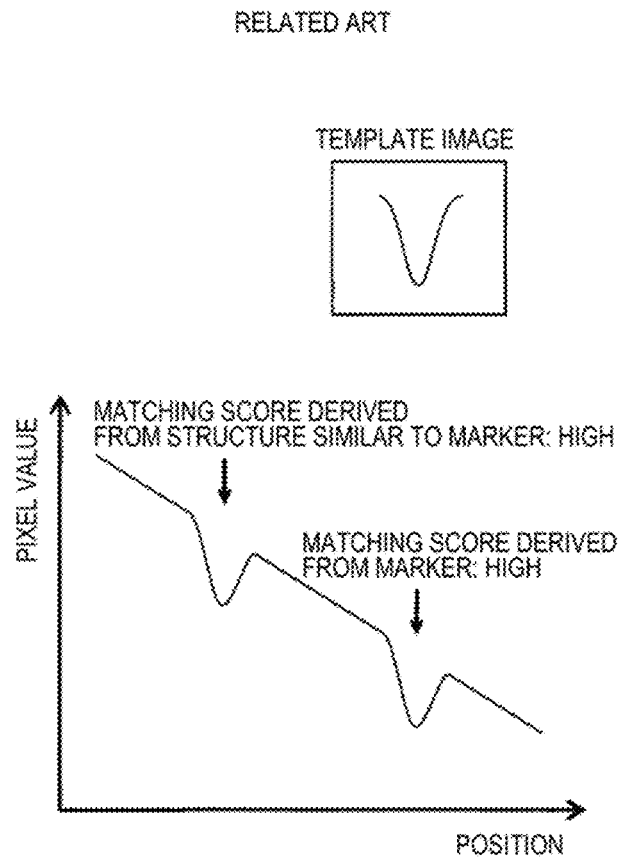
[FIG. 5]
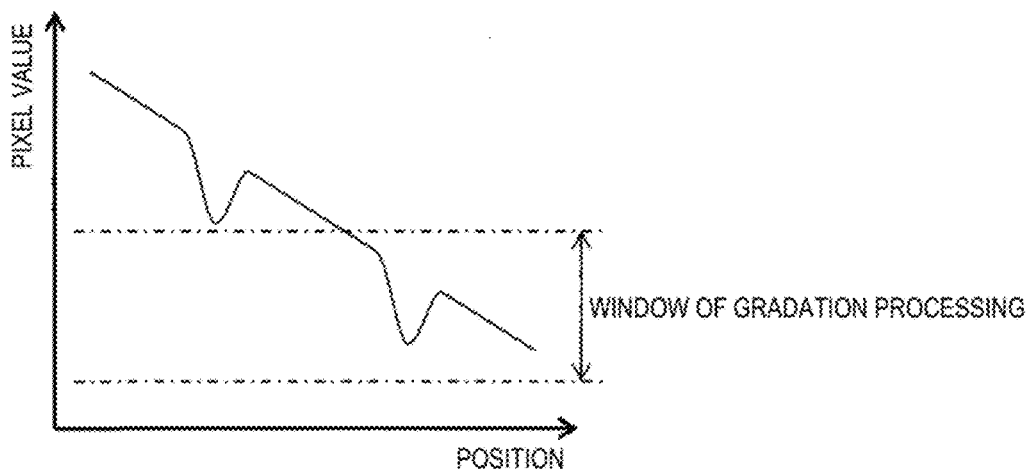

[FIG. 6A]
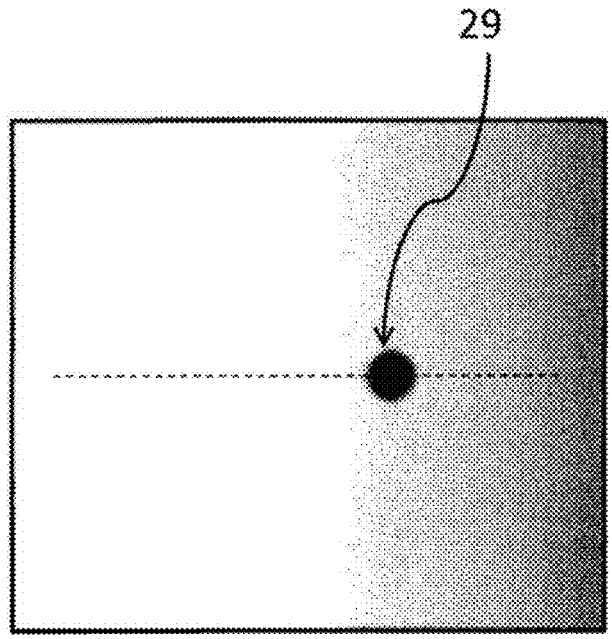
[FIG. 6B]
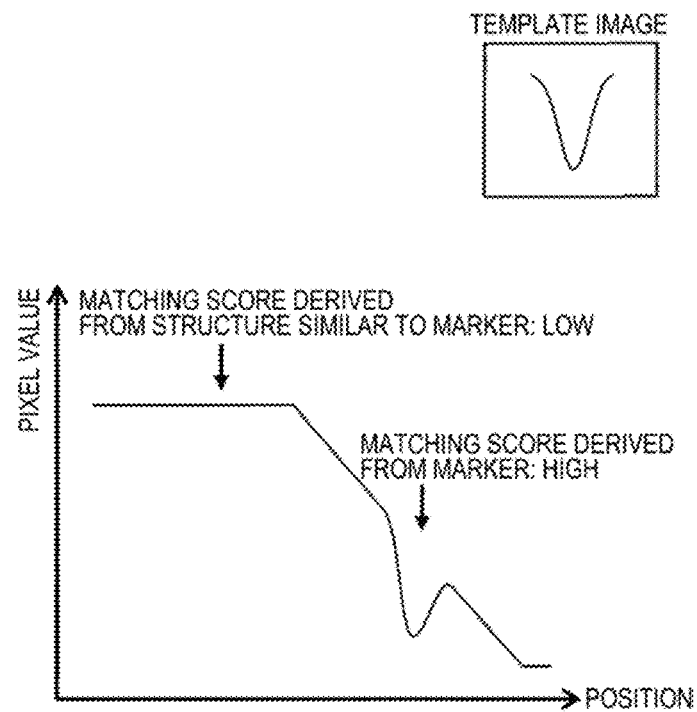

[FIG. 7]
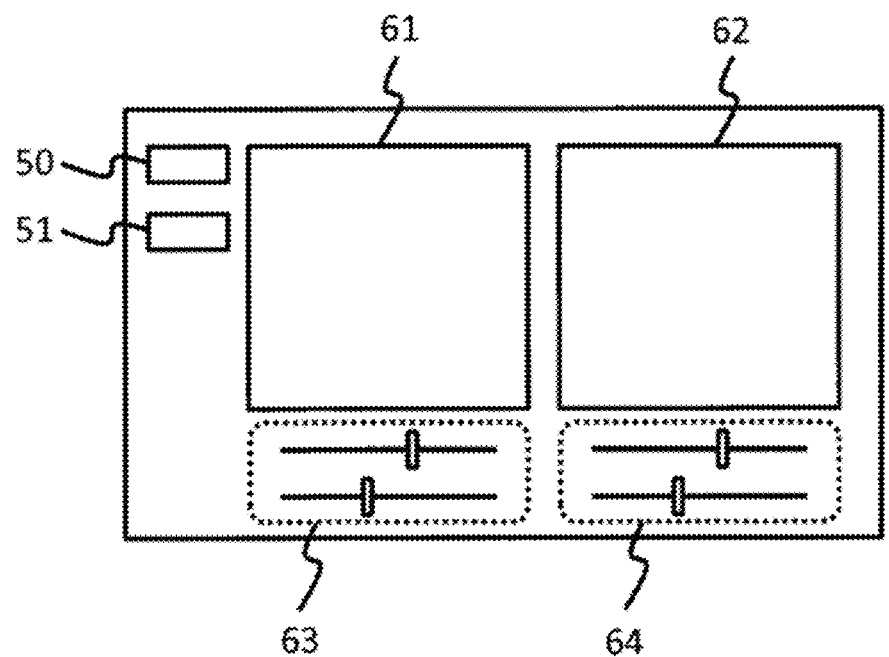
[FIG. 8A]
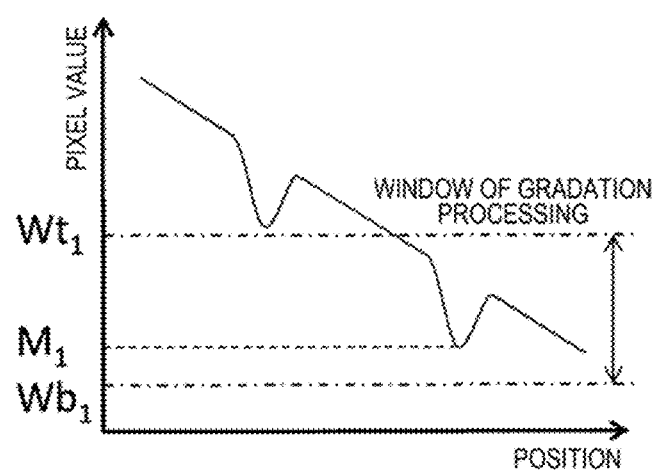

[FIG. 8B]
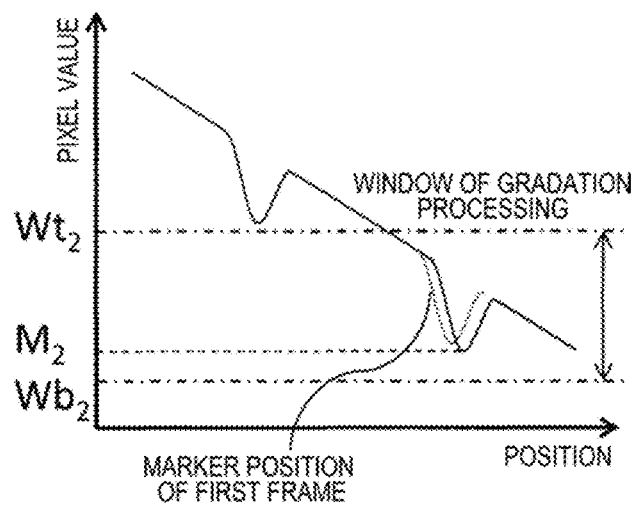
[FIG. 8C]
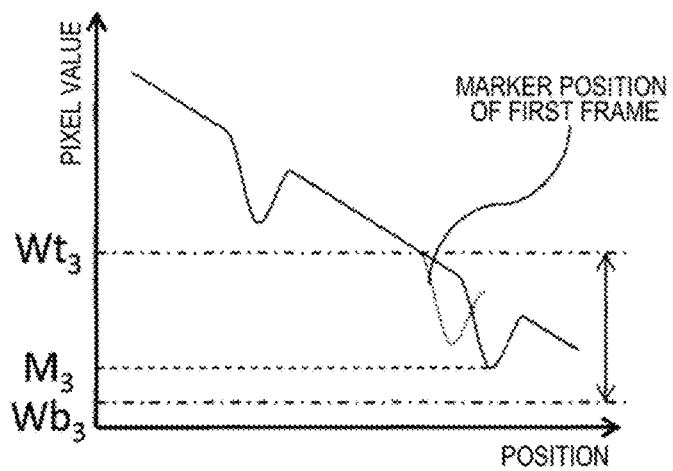

TUMOR TRACKING APPARATUS AND IRRADIATION SYSTEM

TECHNICAL FIELD

The present invention relates to an irradiation system for irradiating an affected part such as a tumor with radiation such as charged particles or X-rays to treat the affected part and a tumor tracking apparatus suitable for such an irradiation system.

BACKGROUND ART

As an example of a tumor tracking irradiation apparatus capable of automatically calculating a position of a tumor moving around in a trunk of a body in real time and ensuring substantially necessary accuracy without depending on absolute accuracy of a mechanical system, PTL 1 discloses a tumor tracking irradiation apparatus including: an imaging device that simultaneously images a fiducial marker embedded in the vicinity of the tumor from the first and second directions to obtain first and second captured images; an image input recognition processing unit that executes template matching by normalized cross-correlation in which a template image of the fiducial marker, which is registered in advance, is applied to digitized first and second captured images, at a real time level of a predetermined frame rate and calculates first and second two-dimensional coordinates of the fiducial marker based on first and second image transformation matrices; a central processing unit that calculates three-dimensional coordinates of the fiducial marker based on the calculated first and second two-dimensional coordinates; and an irradiation control unit that controls treatment beam irradiation of linac based on the calculated three-dimensional coordinates of the fiducial marker.

CITATION LIST

Patent Literature

PTL 1: Japanese Patent No. 3053389

SUMMARY OF INVENTION

Technical Problem

A method of irradiating a patient having cancer or the like, with radiation such as charged particles or X-rays is known. Examples of charged particles include proton beam and carbon ion beam. An irradiation system used for this irradiation forms a dose distribution suitable for a shape of a target such as a tumor in the body of a patient fixed on a patient bed called couch.

However, when a target such as a tumor moves due to respiration or the like, accurate irradiation becomes difficult. Therefore, it has recently been realized to perform gated irradiation that irradiation is performed only when the target is in a predetermined range (gating window).

The above-described PTL 1 discloses a method called tumor tracking irradiation that gated irradiation is performed based on a position of a marker embedded in the vicinity of an affected part.

The marker used for gated irradiation as described in PTL 1 is, for example, a metal sphere having a diameter of approximately 2 mm.

In the tumor tracking irradiation, gated irradiation is performed based on the position of an object to be tracked such as the marker embedded in the vicinity of the affected part and the target itself. The position of the object to be tracked such as the marker is measured using a captured image obtained using X-rays in intersecting two directions. The position of the object to be tracked in the captured image is detected by a method called template matching.

The template matching is a method in which an image of the object to be tracked, which is prepared in advance and called template image is compared with the captured image and a pattern closest to the template image is detected in the captured image. A position, at which two lines connecting the position on the X-ray imaging device that shows the object to be tracked and imaging X-ray generators are closest to each other, is regarded as a position where the object to be tracked exists. When performing the template matching, the captured image and the template image are compared with each other to evaluate similarity such as normalized cross correlation as a matching score.

The present inventors have found that, in the template matching as used in the technique disclosed in PTL 1 described above, when a structure similar to the object to be tracked (non-object to be tracked) appears in the vicinity of the object to be tracked, even in a case where a range of pixel values of the non-object to be tracked is different from the range of pixel values of true object to be tracked, there are problems that a location of the non-object to be tracked also has high matching score and a structure which is non-object to be tracked is erroneously detected as the object to be tracked.

The present invention provides a tumor tracking apparatus and an irradiation system which are capable of tracking an object to be tracked without erroneous detection, even in a case where a structure similar to the object to be tracked is in the vicinity of the object to be tracked, in tumor tracking.

Solution to Problem

The present invention includes a plurality of means for solving the problems described above. However, for example, there is provided a tumor tracking apparatus including: an X-ray imaging apparatus that captures an image of an object to be tracked; and a tumor tracking control device that determines a position of the object to be tracked from a captured image that is imaged by the X-ray imaging apparatus, in which the tumor tracking control device performs windowing process on the captured image, and determines the position of the object to be tracked using the captured image after the windowing process.

Advantageous Effects of Invention

According to the present invention, frequency of erroneous detection of an object to be tracked can be reduced.

BRIEF DESCRIPTION OF DRAWINGS

FIG. 1 is an overall configuration diagram of an irradiation system.

FIG. 2 is a conceptual diagram illustrating that a tumor tracking apparatus acquires a captured image.

FIG. 3 is a conceptual diagram illustrating that the tumor tracking apparatus calculates a position of a marker from the captured image.

FIG. 4A is a conceptual diagram showing a marker position determination method in a general method for comparison.

FIG. 4B is a diagram showing a distribution of pixel values on a dotted line in FIG. 4A in a general method for comparison.

FIG. 5 is a conceptual diagram showing a method of setting a window of windowing process in a first embodiment of the present invention.

FIG. 6A is a conceptual diagram showing a marker position determination method in the first embodiment.

FIG. 6B is a diagram showing a distribution of pixel values on a dotted line in FIG. 6A in the first embodiment.

FIG. 7 is a conceptual diagram showing a screen of a console in the first embodiment.

FIG. 8A is a conceptual diagram showing a method of correcting a window of windowing process in a third embodiment.

FIG. 8B is a conceptual diagram showing the method of correcting the window of the windowing process in the third embodiment.

FIG. 8C is a conceptual diagram showing the method of correcting the window of the windowing process in the third embodiment.

DESCRIPTION OF EMBODIMENTS

Hereinafter, embodiments of a tumor tracking apparatus and an irradiation system of the present invention will be described with reference to the drawings.

Embodiment 1

Embodiment 1 of the tumor tracking apparatus and the irradiation system of the present invention will be described with reference to FIGS. 1 to 7.

The tumor tracking apparatus of the present invention can be applied to an irradiation system such as an X-ray irradiation system, a proton beam irradiation system, or a particle beam irradiation system in which a target is irradiated with heavy ions such as carbon ions. In the present embodiment, as an example, a proton beam irradiation system using proton as radiation with which irradiation is performed as shown in FIG. 1 will be described.

In FIG. 1, the proton beam irradiation system as one embodiment of the present invention includes a proton beam generator 10, a beam transport system 20, an irradiation nozzle 22, a tumor tracking apparatus 38, a couch 27, a control device 40, and the like. Among them, an irradiation device includes the proton beam generator 10, the beam transport system 20, and the irradiation nozzle 22.

The proton beam generator 10 has an ion source 12, a linac 13, and a synchrotron 11. The synchrotron 11 includes a bending magnet 14, a quadrupole magnet (not shown), an RF acceleration apparatus 18, an RF extraction apparatus 19, an extraction deflector 17, and the like. The ion source 12 is connected to the linac 13. The linac 13 is connected to the synchrotron 11. In the proton beam generator 10, the proton beam generated from the ion source 12 is preliminarily accelerated by the linac 13 and is injected to the synchrotron 11. The proton beam further accelerated by the synchrotron 11 is extracted to the beam transport system 20.

The beam transport system 20 includes a plurality of bending magnets 21 and quadrupole magnets (not shown), and is connected to the synchrotron 11 and the irradiation nozzle 22. In addition, a part of the beam transport system 20 and the irradiation nozzle 22 are installed in a cylindrical rotating gantry 25 and can rotate together with the rotating gantry 25. The proton beam extracted from the synchrotron 11 is focussed by the quadrupole magnet while passing through the beam transport system 20, and is changed in direction by the bending magnet 21 to enter the irradiation nozzle 22.

The irradiation nozzle 22 includes two pairs of a scanning magnet, a dose monitor, and a position monitor (all not shown). The two pairs of scanning magnets are installed in mutually orthogonal directions, and it is possible to bend the proton beam so that the proton beam reaches a desired position in a plane perpendicular to a beam axis at a position of the target. The dose monitor measures the amount of proton beam with which irradiation is performed. The position monitor can detect the position where the proton beam has passed. The proton beam that has passed through the irradiation nozzle 22 reaches the target inside an irradiation object 26. When treating a patient having cancer or the like, the irradiation object 26 represents a patient, and the target represents a tumor or the like.

A bed on which irradiation object 26 is placed is called the couch 27. The couch 27 can move in three axes of orthogonal directions, based on an instruction from the control device 40, and further can rotate around the respective axes. According to these movements and rotations, the position of the irradiation object 26 can be moved to a desired position.

The control device 40 is connected to the proton beam generator 10, the beam transport system 20, the irradiation nozzle 22, the tumor tracking control device 41, the couch 27, the storage device 42, the console 43, and the like, and controls these devices.

The tumor tracking apparatus 38 includes: two pairs of X-ray imaging apparatuses each of which includes an imaging X-ray generator 23A and an X-ray imaging device 24A which captures a captured image A 61 of a marker 29, and an imaging X-ray generator 23B and an X-ray imaging device 24B which captures a captured image B 62 of the marker 29; and the tumor tracking control device 41.

Two sets of the imaging X-ray generator 23A and the X-ray imaging device 24A and the imaging X-ray generator 23B and the X-ray imaging device 24B are installed such that paths of the respective X-rays intersect to each other. It is preferable that the two pairs of the imaging X-ray generators 23A and 23B and the X-ray imaging devices 24A and 24B are installed in directions orthogonal to each other, but they may not be orthogonal to each other. In addition, the imaging X-ray generators 23A and 23B and the X-ray imaging devices 24A and 24B do not necessarily have to be disposed inside the rotating gantry 25 and may be disposed at a fixed location such as a ceiling or a floor.

The tumor tracking control device 41 computes the position of the marker 29 based on the signal input from the X-ray imaging apparatus, determines whether or not to permit extraction of the proton beam based on the position of the marker 29, and transmits a signal permitting or not permitting the irradiation of the proton beam to the control device 40.

More specifically, as shown in FIG. 2, the tumor tracking control device 41 irradiates the marker 29 with the X-rays generated from the imaging X-ray generator 23A, and measures the two-dimensional dose distribution of X-rays that have passed through the marker 29 by the X-ray imaging device 24A to image the marker 29. Also, the tumor tracking control device 41 irradiates the marker 29 with the X-rays generated from the imaging X-ray generator 23B, and measures the two-dimensional dose distribution of the X-rays that have passed through the marker 29 by the X-ray imaging device 24B to image the marker 29. The tumor tracking control device 41 computes the three-dimensional position of the marker 29 embedded in the irradiation object 26 from the acquired two captured images, and based on the results, determines whether or not to permit the extraction of the proton beam based on the position of the marker 29. For example, the tumor tracking control device 41 determines whether or not the position of the target obtained from the position of the marker 29 is within a pre-specified gating window (irradiation permission range), and in a case where it is determined that the position of the target is within the gating window, a gate-on signal is transmitted to the control device 40 to permit the extraction. On the other hand, in a case where it is determined that the position of the target is not within the gating window, the gate-off signal is transmitted not to permit the extraction.

Acquisition of the captured images by X-ray imaging apparatus is, for example, performed at certain intervals of 30 Hz. In the acquired captured image, the marker 29 embedded in the body is shown. The position within the irradiation object 26 of the marker 29 is specified by template matching with the template image of the marker 29, which is prepared in advance. When searching the entire range of the captured image, it takes time to search. Therefore, the position of the marker 29 is searched only within the range of the predetermined size centered on the position of the marker 29 in the previous captured image.

FIG. 3 shows a line 28A connecting the position of the marker 29 on the X-ray imaging device 24A, which is detected by template matching and the imaging X-ray generator 23A and a line 28B connecting the position of the marker 29 on the X-ray imaging device 24B and the imaging X-ray generator 23B. These two lines intersect ideally at one point, and the intersection point is a position at which marker 29 exists.

However, practically, the two lines usually do not intersect but are twisted, by being affected by the accuracy of template matching or an installation error of the X-ray imaging apparatus. A common perpendicular can be drawn at the position where the two lines having the twisted relation are closest to each other. This common perpendicular is called a common perpendicular 30. In template matching, a middle point of the common perpendicular 30 is regarded as the position of the marker 29.

Here, in a case where the marker 29 is not correctly detected on at least one captured image, the common perpendicular becomes longer. Using this, in a case where the length of the common perpendicular 30 exceeds a preset threshold value, the tumor tracking control device 41 assumes that there is a high possibility that the marker 29 cannot be correctly detected, and transmits the gate-off signal to the control device 40 to stop the irradiation with the proton beam, even in a case where the position of the marker 29 is within the gating window.

The tumor tracking control device 41 of the present embodiment is characterized by a method of detecting the marker 29. In template matching, the template image of the marker 29, which is prepared in advance, is compared with the captured image to calculate the similarity with the template image, called a matching score. For matching score, the similarity such as normalized cross correlation is used. The higher matching score represents that the captured image being searched matches with the template image.

In a general method, a position at which the matching score is highest, within the search range of the captured image is detected as the position of the marker 29.

Here, if the relative distribution shape of the pixel value is similar to that of the template image, the matching score such as normalized cross correlation has high similarity even if the absolute value of pixel value is different. Therefore, when there is a part of a structure 39 similar to the marker 29 in a search region, the matching score of the position becomes high. Thus, it became clear that there is a possibility of mistaking the place as marker 29.

A general method will be described specifically with reference to FIGS. 4A and 4B. FIG. 4A shows the captured image in a case where the structure 39 similar to the marker 29 is in the vicinity of the marker 29, and FIG. 4B shows the distribution of the pixel value of the captured image on the dotted line shown in FIG. 4A. The actual template image is a two-dimensional image, but FIG. 4A simply shows a template image with a one-dimensional pixel value distribution.

As shown in FIGS. 4A and 4B, in the template matching, the similarity between the distribution of the pixel value of the captured image and the template image is evaluated. However, in a case of using the matching score in which the result is not affected by the absolute value of pixel value like the normalized cross correlation, the part of the structure 39 similar to the marker 29 as shown in FIG. 4A also has a change in the pixel value similar to a template, as shown in FIG. 4B. Therefore, the matching score becomes high. In such a case, there is a concern that a part of the structure 39 similar to the marker 29 may be erroneously detected as the marker 29.

Therefore, in the tumor tracking control device 41 of the present embodiment, in order to prevent the structure 39 similar to the marker 29 having a different absolute value of the pixel value from being erroneously detected, windowing process is performed on the captured image and then the position of the marker 29 is determined. In the present embodiment, "windowing process" refers to imaging processing in which a specific pixel value range (window) is set, a pixel greater than the pixel value of the window upper limit is converted to the upper limit pixel value, and a pixel smaller than the pixel value of the window lower limit is converted to the lower limit pixel value.

An operator sets the window of the windowing process as shown in FIG. 5. The setting of the window may be performed by the operator operating the console 43, and setting values may be stored in advance in the storage device 42 for each irradiation field of the irradiation object 26 which is irradiated with the proton beam, and the stored setting values may be applied. In the present embodiment, a method of setting the window by the operator operating the console 43 will be described. The details will be described later.

A captured image obtained by performing the windowing process on the captured image shown in FIG. 4A is shown in FIG. 6A, and a distribution of pixel values on the dotted line of the captured image after performing the windowing process shown in FIG. 6A is shown in FIG. 6B. As shown in FIG. 6A, since the pixel value of the structure 39 similar to the marker 29 is outside the window of the windowing process, the structure 39 similar to the marker 29 is not seen in the captured image after the windowing process. Therefore, as shown in FIG. 6B, the region outside the window of the windowing process becomes to have uniform pixel value, and the matching score by pattern matching decreases. Therefore, it is possible to reduce the possibility of erroneously detecting the structure 39 similar to the marker 29 as the marker 29.

The proton beam irradiation system of the present embodiment described above employs an irradiation method called a spot scanning method. The spot scanning method is a method of forming a dose distribution that matches the target shape by aligning the dose distributions formed by fine proton beams. The proton beam has characteristics that the proton beam advances while losing energy in the body and the energy loss becomes maximum immediately before stopping. The shape of the dose distribution due to the energy loss is called Bragg-curve and has a peak at the end of a range. A depth at which the proton beam forms the peak can be adjusted by changing the energy of the proton beam. Also, the dose distribution shape in a direction perpendicular to a beam axis formed by the proton beam is roughly a normal distribution. The position at which the dose distribution in the direction perpendicular to the beam axis is formed can be adjusted by scanning the proton beam with a scanning magnet. It is possible to form a uniform dose distribution at the entire of the target by combining change in energy and scanning with the scanning magnet.

Returning to FIG. 1, the storage device 42 stores parameters for irradiation, which is created by a treatment planning system or the like, and the control device 40 receives necessary information from the storage device 42 before the irradiation.

The console 43 is connected to the control device 40 or the tumor tracking control device 41, and displays information on the screen based on the signal acquired from the control device 40 or the tumor tracking control device 41. In addition, the console 43 receives input from an operator operating the proton beam irradiation system and transmits various control signals to the control device 40 and the tumor tracking control device 41. For example, the console 43 displays a tracking status of the captured image or the marker 29 obtained by the X-ray imaging apparatus. In addition, parameters necessary for tracking the marker 29 can be set from the console 43.

FIG. 7 shows a screen for tumor tracking related to the tumor tracking control device 41, which is displayed on the console 43. As shown in FIG. 7, the captured image A 61 obtained from the X-ray imaging device 24A and the captured image B 62 obtained from the X-ray imaging device 24B are displayed on the screen displayed on the console 43. Further, a window setting unit 63 for inputting a pixel value range for performing the windowing process on the captured image A 61 and a window setting unit 64 for inputting a pixel value range for performing the windowing process on the captured image B 62 are displayed on the screen. The tumor tracking control device 41 performs the windowing process based on the pixel value range input by the window setting units 63 and 64 displayed on the console 43.

In addition, FIG. 7 shows a slide bar for setting a window level and a window width as a window setting method for specifying the pixel value range for performing the windowing process, but it is possible to adopt another setting means. As another setting means, for example, a slide bar for setting a maximum pixel value and a minimum pixel value of the window, or a function for directly inputting the values as numerical values is considered. Depending on the change of the window setting of the operator, the display of the captured image A 61 or the captured image B 62 is changed. While watching the captured image A 61 and the captured image B 62 on screen, the operator adjusts the window of the windowing process so that the marker 29 becomes easy to see.

Next, a procedure for a case of irradiation with proton beam will be described.

First, the irradiation object 26 is fixed on the couch 27. Thereafter, the couch 27 is moved to move the irradiation object 26 to the planned position in advance. At this time, by capturing an image using an X-ray imaging apparatus, it is confirmed that the irradiation object 26 has moved to the planned position in advance.

When an irradiation preparation button on the console 43 is pressed by the operator, the control device 40 reads information on a rotating gantry angle, energy, and spot from the storage device 42. In accordance with the read rotating gantry angle, the operator presses the rotating gantry rotation button on the console 43 to rotate the rotating gantry 25.

After rotating the rotating gantry 25, the operator presses an imaging start button 50 on the console 43 to cause the tumor tracking control device 41 to start X-ray imaging. The operator watches two captured images corresponding to the two X-ray imaging apparatuses and adjusts the window of the windowing process so that the marker 29 becomes easy to see. The window is set by the operator operating the window setting units 63 and 64 displayed on the console 43.

After the windowing process is completed, the operator starts to track the marker 29 on each captured image by selecting the marker 29 to be tracked on screen. The template matching is used for tracking the marker 29. In the template matching, a position that best matches the pattern of an image of the marker 29, which is registered as the template image in advance is searched on the captured image. A position at which the matching score is highest on the respective captured images is detected as the marker 29 and tracked.

After confirming the start of tracking on the two captured images corresponding to the two X-ray imaging apparatuses, the gating window is set and the gating start button 51 is pressed. By pressing the gating start button 51, if the position of the marker 29 is within the gating window, the gate-on signal is transmitted from the tumor tracking control device 41 to the control device 40. In addition, in a case where the operator confirms the screen of the console 43 and determines that it is not tracking the intended marker 29, the operator can also correct this.

When an irradiation start button on the console 43 is pressed by the operator, the control device 40 accelerates the proton beam up to first irradiation energy is performed, based on information on energy or a spot, which is read from the storage device 42.

Specifically, the control device 40 controls the ion source 12 and the linac 13, preliminarily accelerates the proton beam generated from the ion source 12 by linac 13, and causes the proton beam to be injected to synchrotron 11.

Next, the control device 40 controls the synchrotron 11 to accelerate the proton beam up to the first irradiation energy. The proton beam circulating in the synchrotron 11 is accelerated by the radio frequency wave from the RF acceleration apparatus 18. The control device 40 controls the excitating current of the bending magnet 21 and the quadrupole magnet of the beam transport system 20 so that the proton beam having the first irradiation energy can reach the irradiation nozzle 22 from the synchrotron 11. In addition, the excitating current of two scanning magnets in the irradiation nozzle 22 is set so that proton beam reaches the spot position irradiated first, in spot information from the storage device 42.

After these settings are completed, if the control device 40 receives the gate-on signal from the tumor tracking control device 41, the irradiation of the proton beam is started. In addition, if the gate-off signal has been received, the control device waits until receiving the gate-on signal.

After receiving the gate-on signal, the control device 40 applies radio frequency wave to the RF extraction apparatus 19 to start extraction of the proton beam. When the radio frequency wave is applied to the RF extraction apparatus 19, a part of the proton beam circulating in the synchrotron 11 passes through the extraction deflector 17, passes through the beam transport system 20, and reaches the irradiation nozzle 22. The proton beam that has reached irradiation nozzle 22 is scanned by two scanning magnets, passes through the dose monitor and the position monitor, reaches the target of the irradiation object 26, and forms a dose distribution. The irradiation amount for each spot is registered in the spot information from the storage device 42. When the irradiation amount measured by the dose monitor reaches the value registered in the spot information, the control device 40 controls the extraction RF and stops the extraction of the proton beam. After the proton beam is extracted, the control device 40 calculates the reaching position of the proton beam at the target position from the positional information of the proton beam, which is measured by the position monitor and confirms that the reaching position matches the position registered in the spot information.

Since the control device 40 irradiates the next spot, the excitating current of the scanning magnet is set so that the proton beam reaches the position registered in the spot information. After completing the setting, if the gate-on signal is continued to be received, the control device 40 controls the extraction RF to start the extraction of the proton beam. If the gate-off signal is received, the control device waits until the gate-on signal is received. If the gate-off signal is received during the irradiation at a certain spot, the proton beam is continued to be extracted until the irradiation of the spot which is being irradiated is completed.

When the irradiation of the spot is repeated and the irradiation of the spot to be irradiated with the first energy is all completed, the control device 40 controls the synchrotron 11 to decelerate the proton beam and starts preparation for irradiation with the proton beam having next energy. The control device 40 controls the ion source 12 and the linac 13 to inject the proton beam to the synchrotron 11, and controls synchrotron 11 to accelerate the proton beam up to the second energy, similar to the case of the first energy. The control device 40 controls the beam transport system 20 and the scanning magnet to continue the irradiation of the spot.

The above operation is repeated, and all the spots read from the storage device 42 are irradiated. When the irradiation is completed, the irradiation completion signal is transmitted from the control device 40 to the tumor tracking control device 41. The tumor tracking control device 41 that has received the irradiation completion signal controls the imaging X-ray generators 23A and 23B to stop the imaging of X-rays.

In a case of irradiating the target from a plurality of directions, after changing the angle of the rotating gantry 25 and the position of the couch 27, the operator presses the irradiation preparation button and repeats irradiation of the proton beam in the same manner.

Hereinafter, effects of the present embodiment will be described.

In Embodiment 1 of the tumor tracking apparatus and the irradiation system of the present invention described above, a tumor tracking control device 41 performs windowing process on a captured image A 61 and a captured image B 62, measures a position of a marker 29 using the captured image A 61 and the captured image B 62 after performing the windowing process, and generates a signal for controlling irradiation with radiation based on the position of the marker 29.

According to the configuration as above, even in a case where there is the structure 39 similar to the marker 29 in the vicinity of the marker 29, the tumor tracking apparatus 38 can continuously track the marker 29 without losing. By reducing the frequency of losing the marker 29 in this manner, it is possible to omit the trouble for the operator to detect the marker 29 again in the tumor tracking apparatus 38 when the marker 29 is lost, and thus it is possible to shorten the irradiation time. In addition, by shortening the irradiation time, it is possible to reduce the number of imaging times of X-rays and also to reduce the exposure dose of the irradiation object 26. Further, since the marker 29 can be tracked even in a case where the quality of the captured image deteriorates, the marker 29 can be tracked even if the intensity of X-rays in the X-ray imaging apparatus is reduced, and it is possible to reduce the exposure dose of the irradiation object 26, in the same manner.

In addition, the window setting units 63 and 64 for inputting a pixel value range for performing windowing process are further provided, and the tumor tracking control device 41 performs the windowing process based on the pixel value range input from the window setting units 63 and 64. Therefore, the operator can determine the pixel value range for performing the windowing process while confirming the captured image displayed on the console 43 and can perform the windowing process with high accuracy. Therefore, it is possible to further reduce the frequency of losing the marker 29.

Further, the X-ray imaging apparatus including the two imaging X-ray generators 23A and 23B and two X-ray imaging devices 24A and 24B captures the captured image A 61 and the captured image B 62 of the marker 29 from two different directions, and thus it is possible to obtain the three-dimensional position of the marker 29 in the irradiation object 26 with high accuracy.

In addition, as the windowing process, a specific pixel value range is set, pixels greater than the pixel value range are converted to the upper limit pixel value of the range, and pixels smaller than the pixel value range are converted to the lower limit pixel value of the range. Accordingly, it is possible to further reduce the possibility of erroneously detecting the structure 39 similar to the marker 29 as the marker 29.

In addition, the tumor tracking apparatus 38 outputs a signal that allows the control device 40 to emit radiation when the position of the marker 29 is within a pre-specified range. Accordingly, it is possible to increase irradiation accuracy with the radiation on the target inside the irradiation object 26.

Embodiment 2

Embodiment 2 of the tumor tracking apparatus and the irradiation system of the present invention will be described. The same reference numbers are given to the same configurations as those in FIGS. 1 to 7, and the explanation thereof is omitted. This also applies to the following embodiments.

A difference between the tumor tracking apparatus and the irradiation system according to the second embodiment of the present invention and those of the first embodiment is the method of setting the window of windowing process to be performed on the captured image.

In general, in radiation therapy, the same irradiation is repeated over several days in order to treat one patient. Here, a patient's body shape does not change significantly during the several days of the treatment day. Therefore, even if the treatment days are different, if the same irradiation angle is used, the pixel value of captured image acquired for tracking the marker 29 does not change significantly. Therefore, in the present embodiment, the tumor tracking control device 41 sets the pixel value range in windowing process using the window of windowing process set at the time of treatment up to the previous day, and performs windowing process on the day of irradiation using this setting. Hereinafter, specific description will be made.

First, during treatment on the first day, the operator sets the window of the windowing process by the same method as the first embodiment. At this time, the information of the window set for each irradiation field is stored in the storage device 42.

On the second day of treatment, when the operator presses the imaging start button 50 on the console 43 to cause the tumor tracking control device 41 to start the X-ray imaging, the captured image for which the window of the windowing process of the previous day has been set is displayed on the screen, based on the information stored in the storage device 42. At this time, the operator confirms the captured image and adjusts the window as necessary. Information on the window on the second day is also stored in the storage device 42. Treatment after completion of the windowing process is performed in the same manner as in the first embodiment.

Similarly on and after the third day, the window of the previous day is set to perform the windowing process on the captured image, based on the information stored in the storage device 42.

The configuration other than the above is substantially the same as the tumor tracking apparatus and the irradiation system of Embodiment 1. In addition, a method of generating the gate signal based on the position of the marker 29 and controlling the irradiation and stop of the treatment beam is the same as those in Embodiment 1. Therefore, a detailed description will be omitted.

Also in the tumor tracking apparatus and the irradiation system of the present embodiment, the same effect as the tumor tracking apparatus and the irradiation system of the above-described Embodiment 1 can be obtained.

In addition, the tumor tracking control device 41 stores the parameter obtained by previous windowing process on the captured image A 61 and captured image B 62 obtained by imaging the marker 29 in the storage device 42, and determines the pixel value range in the windowing process based on information in the storage device 42. Accordingly, it is possible to promptly start the irradiation on and after the second day during which the irradiation condition does not substantially change and it is possible to further shorten the irradiation time.

In the above description, a case where the window setting on the previous day is handed over as it is at the time of performing the windowing process on and after the second day has been described, but for example, an average value from the first day to the previous day may be set, and moving average of last several days may be set.

Embodiment 3

Embodiment 3 of the tumor tracking apparatus and the irradiation system of the present invention will be described with reference to FIGS. 8A to 8C.

A difference between the tumor tracking apparatus and the irradiation system according to a third embodiment of the present invention and those of the first embodiment and the second embodiment is the method of setting the window of windowing process to be performed on the captured image.

As described above, the marker 29 used for tracking a tumor also moves inside the body due to respiration and pulsation of the patient as with the target. During such movement, in a case where the marker 29 moves to the back side of a portion where the water-equivalent thickness is large such as bone, as seen from the irradiation direction of the imaging X-ray, a transmission amount of the imaging X-ray may decrease. In such a case, the pixel value of the marker 29 decreases. On the contrary, in a case where the marker 29 moves to a portion where the water-equivalent thickness is small, the transmission amount of the imaging X-ray increases. Accordingly, the pixel value of the marker 29 increases.

Thus, the pixel value of the marker 29 changes with the movement of the marker 29. However, in a case where the window of the windowing process is fixed, there is a possibility that the pixel value of the marker 29 is outside of the range of the window of the windowing process due to the movement of the marker 29. In a case where the pixel value of the marker 29 appears outside the window of the windowing process, the matching score decrease. Therefore, there is a concern of erroneously detecting a three-dimensional position of the marker 29.

Therefore, in the present embodiment, the window of the windowing process is adjusted based on the captured images A 61, the captured image A 61 obtained by imaging the marker 29 before the captured image B 62, and the captured image B 62, which are evaluation targets. Specific description will be made with reference to FIGS. 8A to 8C. FIG. 8A is a diagram showing the image at the start of the tracking of the marker 29. FIG. 8B is a diagram showing the image of the second frame from the start of the tracking of the marker 29. FIG. 8C is a diagram showing the image of the third frame from the start of the tracking of the marker 29.

First, in order to start the tracking of the marker 29, the operator presses the imaging start button 50 on the console 43 to cause the tumor tracking control device 41 to start X-ray imaging. The operator watches two captured images corresponding to the two X-ray imaging apparatuses and operates the window setting units 63 and 64 displayed on the console 43 to adjust the window of the windowing process so that the marker 29 becomes easy to see.

After the windowing process is completed, the operator starts to track the marker 29 on each captured image on which the windowing process has been performed, by selecting the marker 29 to be tracked on screen. At the time when the operator selects the marker 29, the tumor tracking control device 41 stores a window upper limit pixel value $Wt_1$, a window lower limit pixel value $Wb_1$, and a peak position pixel value $M_1$ of the marker 29 of the windowing process as shown in FIG. 8A. Hereinafter, the upper limit and the lower limit of the window of the windowing process are respectively represented as $Wt_n$, $Wb_n$, and the peak position pixel value of the marker 29 is represented as $M_n$, in the captured image of the n-th frame from the start of tracking of the marker 29.

For example, for the captured image of the second frame from the start of tracking of the marker 29 as shown in FIG. 8B, the window of the windowing process is equivalent to the captured image of the first frame. That is, the relation of these satisfies $Wt_2=Wt_1$ and $Wb_2=Wb_1$.

As shown in FIG. 8C, for the captured image on and after the third frame from the start of tracking of the marker 29, the pixel values of the upper and lower limits of the window are corrected so as to maintain an interval between the peak and the pixel values of the window as the state of the first frame. That is, relations of $Wt_3=M_2$ ($Wt_1-M_1$) and $Wb_3=M_2-(M_1-Wb^1)$ are satisfied on the captured image of the third frame. That is, for the captured image of the n-th frame, windowing process is performed in a state set as $Wt_n=M_{n-1}+(Wt_1-M_1)$ and $Wb_n=M_{n-1}-(M_1-Wb_1)$.

Also in the present embodiment, the configuration other than the above is substantially the same as the tumor tracking apparatus and the irradiation system of Embodiment 1. In addition, a method of generating the gate signal based on the position of the marker 29 and controlling the irradiation and stop of the treatment beam is the same as those in Embodiment 1. Therefore, a detailed description will be omitted.

Also in the tumor tracking apparatus and the irradiation system of the present embodiment, the same effect as the tumor tracking apparatus and the irradiation system of the above-described first embodiment can be obtained.

In addition, the tumor tracking control device 41 determines the pixel value range in windowing process based on the information of the captured image A 61, the captured image A 61 obtained by imaging the marker 29 before the captured image B 62, and the captured image B 62, which are targets for windowing process. Accordingly, even in a case where fluctuation of the pixel value of a portion of the marker 29 occurs due to the movement of the marker 29, since the window of the windowing process is corrected according to this, it is possible to further reduce the possibility that the pixel value of the marker 29 is outside the range of the window of the windowing process, that is, the possibility of losing of the marker 29.

In the above description, a case where the operator performs the window setting of the windowing process of the first frame is described. However, even when the automatic setting is made based on the information at the time of treatment up to the previous day as in the second embodiment, the correction of the window shown in the present embodiment is effective.

In addition, in the above description, a case where the upper and lower limits of the window are corrected so as to make the interval between pixel values of the peak and the window constant is described. However, it is not always necessary to keep upper and lower limits of the peak and window to be constant. For example, the lower limit of the window may be fixed, and the upper limit of the window and the pixel value range of the peak may be kept to be constant. In addition, the upper limit of the window may be fixed, and the lower limit of the window and the pixel value range of the peak may be kept to be constant.

In addition, in the above description, a case where the upper and lower limits of the window are corrected so as to make the pixel value interval $Wt_n-Wb_n$ between the upper and lower limits of the peak constant is described, but it is not always necessary to keep $Wt_n-Wb_n$ to be constant, and the upper and lower limits may be corrected in accordance with the movement of the marker 29.

<Others>

The present invention is not limited to the above embodiments, and includes various modified examples. The above embodiments have been described in detail in order to explain the present invention in an easy-to-understand manner, and the present invention is not necessarily limited to those having all the described configurations. In addition, it is also possible to replace a part of the configuration of an embodiment with the configuration of another embodiment, and it is also possible to add a configuration of the other embodiment to the configuration of the embodiment. In addition, it is also possible to add, delete, or replace the other configuration with respect to apart of the configuration of each embodiment.

For example, in the above-described embodiment, a case where the target is imaged using the two X-ray imaging apparatuses has been described as an example, but the X-ray imaging apparatus is not necessarily required to be two. For example, by moving one X-ray imaging apparatus, captured images of the object to be tracked may be captured from two different directions.

In the above-described embodiment, a case where the gated irradiation is performed based on the position of the spherical marker 29 has been described as an example, but the shape of the marker 29 may also be a coil shape. In addition, a case where the object to be tracked is the marker 29 has been described, but the object to be tracked is not limited to the marker 29, and the target may be directly detected without using the marker 29. Alternatively, the object to be tracked may be a high density region within the irradiation object 26, such as a bone such as a rib.

In addition, the irradiation method may be tracking irradiation that tracks the irradiation position based on the position of the marker 29 or the like instead of the gated irradiation. For example, in tracking irradiation of X-rays, the direction of the distribution forming X-ray generator is changed in accordance with the movement of the target, and the irradiation position of the X-ray is changed in accordance with the movement of the target. Also in a case of the particle beam, tracking irradiation can be performed by adjusting the excitating current of the scanning magnet in accordance with the target position.

The imaging X-ray is also a kind of radiation. However, since it is not used for the purpose of forming a dose distribution, in the present specification, the treatment beam is used as a generic term for radiation other than imaging X-ray.

Further, in the above embodiment, the proton beam irradiation system is described as an example, but the irradiation system of the present invention can also be applied to a system that performs irradiation with a particle beam, X-rays, and electron beams other than a proton beam such as a carbon beam in the same manner. For example, in a case of using the X-rays, the irradiation device includes an X-ray generator, a beam transport system, and an irradiation nozzle.

In addition, in a case of a particle beam irradiation device, in addition to the spot scanning method described in the above embodiments, the same applies to a raster scanning irradiation method or a line scanning irradiation method in which irradiation is performed with a fine particle beam without stopping a particle beam. Further, in addition to the scanning method, the present invention can also be applied to an irradiation method in which the distribution of particle beams is expanded and then the dose distribution corresponding to the shape of the target is formed using a collimator or a compensator, such as the wobbler method and the double scattering method.

In addition, in a case of the particle beam irradiation system, the particle beam generator may be a cyclotron in addition to the synchrotron 11 described in the above embodiments.

REFERENCE SIGNS LIST

10: proton beam generator
11: synchrotron
12: ion source

13: linac
14: bending magnet
17: extraction deflector
18: RF acceleration apparatus
19: RF extraction apparatus
20: beam transport system
21: bending magnet
22: irradiation nozzle
23A and 23B: imaging X-ray generator
24A and 24B: X-ray imaging device
25: rotating gantry
26: irradiation object
27: couch
29: marker
30: common perpendicular
38: tumor tracking apparatus
39: structure similar to marker
40: control device
41: tumor tracking control device
42: storage device
43: console
50: imaging start button
51: gating start button
61: captured image A
62: captured image B
63: window setting unit
64: window setting unit

The invention claimed is:

1. A tumor tracking apparatus comprising:
an X-ray imaging apparatus that captures an image of an object to be tracked; and
a tumor tracking control device that determines a position of the object to be tracked from a captured image that is imaged by the X-ray imaging apparatus,
wherein the tumor tracking control device performs windowing process on the captured image, and determines the position of the object to be tracked using the captured image after the windowing process, and
wherein the tumor tracking control device changes a pixel value range of the windowing process, in accordance with a movement of the object to be tracked.

2. The tumor tracking apparatus according to claim 1, further comprising:
a window setting unit that inputs a pixel value range for the windowing process, wherein
the tumor tracking control device performs the windowing process based on a pixel value range input by the window setting unit.

3. The tumor tracking apparatus according to claim 1, wherein
the tumor tracking control device determines a pixel value range in the windowing process, by using a parameter of the windowing process of the object to be tracked, which is stored in a storage device.

4. The tumor tracking apparatus according to claim 1, wherein
the pixel value range is determined by an upper limit pixel value in the pixel value range of the captured image obtained by imaging the object to be tracked before a captured image of a target of the windowing process, a lower limit pixel value of the pixel value range, and a pixel value of a peak position of the object to be tracked.

5. The tumor tracking apparatus according to claim 1, wherein
when the pixel value range is set, the tumor tracking control device converts a pixel greater than an upper limit of the pixel value range to the upper limit pixel value of the pixel value range and converts a pixel smaller than the lower limit of the pixel value range to the lower limit pixel value of the pixel value range.

6. The tumor tracking apparatus according to claim 1, wherein
the tumor tracking control device generates a signal for controlling irradiation with radiation, based on a determined position of the object to be tracked.

7. The tumor tracking apparatus according to claim 1, wherein
the X-ray imaging apparatus captures images of the object to be tracked from two different directions.

8. The tumor tracking apparatus according to claim 1, wherein
the object to be tracked is any of a marker for identifying a target, the target, and a high-density region.

9. An irradiation system comprising:
an irradiation device that irradiates a target with radiation;
an irradiation control device that controls the irradiation device; and
the tumor tracking apparatus according to claim 1, wherein
the irradiation control device controls treatment radiation, based on a signal generated by the tumor tracking apparatus.

10. The irradiation system according to claim 9, wherein
the tumor tracking apparatus outputs a signal that allows the irradiation control device to emit radiation when a position of the object to be tracked is within a pre-specified range.

* * * * *